United States Patent [19]

Tahara et al.

[11] Patent Number: 4,874,759
[45] Date of Patent: Oct. 17, 1989

[54] 5-HYDROXYINDOLE-3-CARBOXYLIC ACID AMIDE COMPOUNDS, PHARMACEUTICAL COMPOSITIONS AND USE

[75] Inventors: Tetsuya Tahara, Nakatsu; Tsuguo Ikebe, Shimoge; Ichiro Hakamada; Osamu Yaoka, both of Nakatsu, all of Japan

[73] Assignee: Yoshitomi Pharmaceutical Industries, Ltd., Osaka, Japan

[21] Appl. No.: 261,836

[22] PCT Filed: Jan. 19, 1988

[86] PCT No.: PCT/JP88/00035
§ 371 Date: Sep. 23, 1988
§ 102(e) Date: Sep. 23, 1988

[87] PCT Pub. No.: WO88/05432
PCT Pub. Date: Jul. 28, 1988

[30] Foreign Application Priority Data

Jan. 23, 1987 [JP] Japan .................... 62-14943

[51] Int. Cl.[4] ............... A61K 31/405; A61K 31/535; C07D 209/42; C07D 413/06
[52] U.S. Cl. ...................... 514/232.5; 514/234.5; 514/235.2; 514/253; 514/269; 514/272; 514/313; 514/314; 514/316; 514/318; 514/322; 514/323; 514/333; 514/338; 514/339; 514/386; 514/387; 514/388; 514/392; 514/394; 514/395; 514/397; 514/404; 514/407; 514/414; 514/419; 544/80; 544/121; 544/122; 544/123; 544/128; 544/130; 544/131; 544/139; 544/140; 544/144; 544/295; 544/296; 544/322; 544/328; 544/331; 544/357; 544/360; 544/363; 544/364; 544/370; 544/371; 544/373; 546/160; 546/162; 546/168; 546/169; 546/171; 546/187; 546/193; 546/194; 546/199; 546/201; 546/256; 546/271; 546/273; 548/301; 548/305; 548/327; 548/328; 548/336; 548/358; 548/362; 548/374; 548/454; 548/492

[58] Field of Search ............... 544/80, 121, 122, 123, 544/128, 130, 131, 139, 140, 144, 295, 296, 322, 328, 331, 357, 360, 363, 364, 370, 371, 373; 546/160, 162, 168, 169, 171, 187, 193, 194, 199, 201, 256, 271, 273; 548/301, 305, 327, 328, 336, 358, 374, 362, 454, 492; 514/232.5, 234.5, 253, 264, 272, 313, 314, 316, 318, 322, 323, 333, 338, 339, 386, 387, 388, 392, 394, 395, 397, 404, 407, 414, 419

[56] References Cited

FOREIGN PATENT DOCUMENTS 188665 8/1988 Japan .

OTHER PUBLICATIONS

Bell et al, *J. Med. Chem.*, vol. 10, pp. 264–266 (1967).

Primary Examiner—Robert W. Ramsuer
Attorney, Agent, or Firm—Wenderoth, Lind & Ponack

[57] ABSTRACT

Hydroxyindole-3-carboxylic acid amide compounds of the general formula:

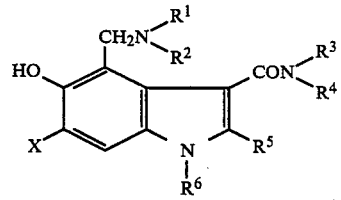

wherein $R^1$, $R^2$, $R^3$ and $R^4$ are, the same or different, respectively a hydrogen atom, an alkyl group, an aryl group, an aralkyl group or a heteroaryl group, or $R^1$ and $R^2$ and/or $R^3$ and $R^4$ are respectively groups which are combined to each other taken together with the adjacent nitrogen atom to form a heterocyclic group, $R^5$ is an alkyl group, $R^6$ is a hydrogen atom, an alkyl group, a cycloalkyl group, an aryl group or an aralkyl group and X is a hydrogen atom, a halogen atom or a lower alkanoyl group, or their acid addition salts.

These compounds are of use as diuretics or a therapeutic medicine for circulation system diseases.

6 Claims, No Drawings

5-HYDROXYINDOLE-3-CARBOXYLIC ACID AMIDE COMPOUNDS, PHARMACEUTICAL COMPOSITIONS AND USE

TECHNICAL FIELD

The present invention relates to 5-hydroxyindole-3-carboxylic acid amide compounds and their acid addition salts which are novel and of use as diuretics or therapeutic medicines for circulation system diseases.

BACKGROUND ART

With an increase in the population of aged people, various diseases of circulation systems, particularly cerebral and cardiac circulation system diseases caused by atroclerosis, hypertension, etc. have become a serious social problem. As the therapeutic medicines for such diseases, useful medicaments are those which have hyperkinemic actions, particularly those which exhibit vasodilating actions on cerebral blood vessels and coronary blood vessels, or those which have diuretic actions.

Also, in recent years, better use have been made of the medicaments which have anti-platelet aggregation actions for the treatment of thrombotic diseases. Furthermore, in view of the fact that leucotrienes which are metabolically produced by 5-lipoxygenase on arachidonic acid cascade possess potent coronary vasospasm, attention has been paid to the relationship between cardiac diseases such as angina pectoris and leukotrienes. Therefore it is said that the compounds which have 5-lipoxygenase-inhibitory actions are of use for the treatment of such circulatory diseases.

In U.S. Pat. No. 2852527 and Journal of Medicinal Chemistry, vol. 10, p. 264 (1967), there are described lower alkyl esters of 2-lower alkyl-5-hydroxy-4-tertiary-aminoindole-3-carboxylic acids which have central nervous system-stimulating actions and hypoglycemic actions.

However, the forementioned known compounds have high toxicity, and there has not been any suggestion about pharmacological actions against circulatory diseases.

In the specification of U.S. Pat. No. 4581355, there are disclosed some species of indole-3-carboxamide compounds, which have 5-lipoxygenase actions, antihypertensive actions or cardiac actions, but these compounds do not exhibit any diuretic actions.

DISCLOSURE OF THE INVENTION

For the purpose of developing compounds which are useful as diuretics, the present inventors have intensively conducted studies to find that novel 5-hydroxyindole-3-carboxylic acid amide compounds and their acid addition salts have antihypertensive actions, cerebral vasodilating actions, coronary vasodilating actions, anti-platelet aggregation actions and/or 5-lipoxygenase-inhibiting actions besides excellent diuretic actions, and that thus they are useful as diuretics, antihypertensive agents and therapeutic agents for cerebral and cardiac circulation system diseases. These findings have resulted in the completion of the present invention.

That is, the present invention relates to 5-hydroxyindole-3-carboxylic acid amide compounds of the general formula:

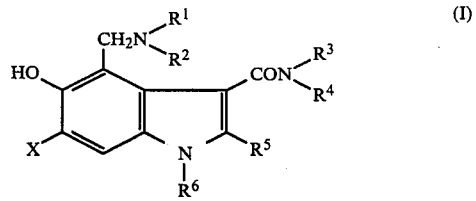

wherein $R^1$, $R^2$, $R^3$ and $R^4$ are, the same or different, independently a hydrogen atom, an alkyl group, an aryl group, an aralkyl group or a heteroaryl group, or $R^1$ and $R^2$ and/or $R^3$ and $R^4$ respectively are combined to each other to form a heterocyclic group as taken together with the adjacent nitrogen atom, $R^5$ is an alkyl group, $R^6$ is a hydrogen atom, an alkyl group, a cycloalkyl group, an aryl group or an aralkyl group and X is a hydrogen atom, a halogen atom or a lower alkanoyl group, or their acid addition salts.

With reference to the above-mentioned substituents, the halogen atom represents chlorine, bromine, fluorine or iodine atom, the alkyl group represents a straight- or branched-chain alkyl having 1 to 8 carbon atoms such as methyl, ethyl, propyl, isopropyl, butyl, isobutyl, tert-butyl, pentyl, isopentyl, neopentyl, hexyl, heptyl, octyl, 2-ethylhexyl or 1,1,3,3-tetramethylbutyl, the lower alkanoyl group represents an alkanoyl having 2 to 5 carbon atoms such as acetyl, propionyl, butyryl, pivaloyl or valeryl, the cycloalkyl group represents a cycloalkyl having 3 to 7 carbon atoms such as cyclopropyl, cyclobutyl, cyclopentyl, cyclohexyl or cycloheptyl, the aryl group represents phenyl, naphthyl or so on, the aralkyl group represents benzyl, phenylethyl, phenylpropyl, phenylbutyl or so on, the heteroaryl group represents pyrazolyl, imidazolyl, pyridyl, furyl, thienyl, pyrimidinyl, quinolyl, benzofuryl, benzothienyl, benzimidazolyl or the like, and said aromatic (hetero) cyclic groups may have on the ring at least one substitutent selected from among halogen atoms (as exemplified by the above-mentioned), alkyl groups (as exemplified by the above-mentioned), alkoxy groups (straight- or branched-chain alkoxy having 1 to 8 carbon atoms such as methoxy, ethoxy, propoxy, isopropoxy, butoxy, isobutoxy, tert-butoxy, pentyloxy, hexyloxy, heptyloxy and octyloxy), trifluoromethyl group, nitro group and amino group. The heterocyclic group formed combinedly as taken together with the adjacent nitrogen atom represents 1-pyrrolidinyl, piperidino, 1-piperazinyl, 4-methyl-1-piperazinyl, 4-(2-hydroxyethyl)-1-piperazinyl, 4-phenyl-1-piperazinyl, 4-diphenylmethyl-1-piperazinyl, morpholino or so on.

As the acid addition salts of the compounds of formula (I), there are mentioned inorganic acid salts such as hydrochloride, hydrobromide, phosphate and sulfate and organic acid salts such as fumarate, maleate, succinate, tartrate, methanesulfonate and pamoate. As such acid addition salts, those which are pharmaceutically acceptable in view of the object of the present invention to provide drugs for human beings are preferred.

As the compounds of formula (I), preferred are the compounds wherein $R^1$ and $R^2$ represents groups which are combined to each other with the adjacent nitrogen atom to form piperidine and among them, more preferable compounds include 4-(5-hydroxy-2-methyl-4-piperidinomethylindol-3-ylcarbonyl)morpholine, 4-(6-bromo-5-hydroxy-2-methyl-4-piperidinomethylindol-3- ylcarbonyl)morpholine, N,N-dibutyl-5-hydroxy-2-methyl-1-(2-phenylethyl)-4-piperidinomethylindole-3-carboxyamide, N,N-dibutyl-5-hydroxy-2-methyl-1-(2-phenylethyl)-4-piperidinomethyl-6-propionylindole-3-carboxamide, N,N-dibutyl-1-hexyl-5-hydroxy-2-methyl-4-piperidinomethyl-6-propionylindole-3-carboxamide, 1,N-dibutyl-5-hydroxy-2-methyl-4-piperidinomethylindole-3-carboxamide, 6-bromo-1,N-dibutyl-5-hydroxy-2-methyl-4-piperidinomethylindole-3-carboxamide, 6-bromo-N-butyl-5-hydroxy-2-methyl-4-piperidinomethylindole-3-carboxamide, 4-[6-bromo-5-hydroxy-2-methyl-1-(2-phenylethyl)-4-piperidinomethylindol-3-ylcarbonyl]morpholine, 4-(6-bromo-1-butyl-5-hydroxy-2-methyl-4-piperidinomethylindol-3-ylcarbonyl)morpholine, N,N-dibutyl-5-hydroxy-2-methyl-4-piperidinomethylindole-3-carboxamide, 6-bromo-N,N-dibutyl-5-hydroxy-2-methyl-4-piperidinomethylindole-3-carboxamide, 1-(6-bromo-5-hydroxy-2-methyl-4-piperidindomethylindol-3-ylcarbonyl)piperidine, and N,N-dibutyl-5-hydroxy-2-methyl-1-phenyl-4-piperidinomethyl-6-propionylindole-3-carboxamide and their acid addition salts.

The compounds of formula (I) of the present invention can be produced by, for example, the following methods.

Method 1

The compounds of formula (I) wherein X is a hydrogen atom can be produced by subjecting the compounds of formula

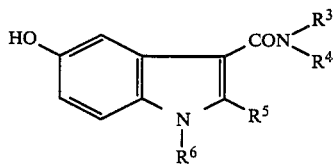

wherein each of the symbols is as defined above, to the Mannich reaction (reviewed in Organic Reactions, vol. 1, p. 303 (1942) or so on).

The reaction proceeds preferably in a solvent inert to the reaction such as methanol, acetic acid or dioxane at room temperature to reflux.

Method 2

The compounds of formula (I) wherein X is a lower alkanoyl group can be produced by subjecting the corresponding compounds of formula (I) wherein X is a hydrogen atom to the Friedel-Crafts reaction.

The reaction can proceed by allowing to react a lower alkanoyl halide with the compound of formula (I) in the presence of a Lewis acid such as aluminum chloride, tin tetrachloride or ferric chloride in a solvent inert to the reaction such as dichloromethane, dichloroethane or nitrobenzene.

Method 3

The compounds of formula (I) wherein X is a halogen atom can be produced by subjecting the corresponding compounds of formula (I) wherein X is a hydrogen atom to halogenation reaction.

The reaction can be conducted with the use of a halogenation agent such as bromine, sulfuryl chloride, perchloryl fluoride and iodine monochloride in a solvent inert to the reaction such as acetic acid, chloroform and carbon tetrachloride.

Also, the compounds of formula (I) wherein X is a halogen atom can be produced by subjecting the corresponding compounds of formula

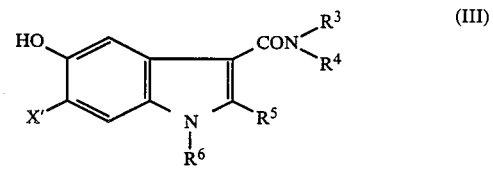

wherein X' is a halogen atom and other symbols are as defined above to the Mannich reaction in the same manner as Method 1 mentioned above.

Method 4

The compounds of formula (I) wherein either $R^1$ or $R^2$ is a hydrogen atom or both $R^1$ and $R^2$ are hydrogen atoms can be produced by respectively synthesizing the compounds of formula (I) wherein either $R^1$ or $R^2$ is benzyl or both $R^1$ and $R^2$ are benzyl, followed by subjecting the synthesized compounds to a conventional debenzylation reaction such as catalytic hydrogenation reaction.

The compounds of formula (I) thus obtained can be converted to the above-described corresponding acid addition salts by the conventional treatment with an inorganic acid such as hydrochloric acid, hydrobromic acid, phosphoric acid or, sulfuric acid or an organic acid such as fumaric acid, maleic acid, succinic acid, citric acid, tartaric acid, methanesulfonic acid or pamoic acid.

The diuretic actions and the actions on circulation systems of the compounds of this invention are described by illustrating the following Pharmacological Experimental Examples.

PHARMACOLOGICAL EXPERIMENTAL EXAMPLE 1

Diuretic action

Male Wistar strain rats (each weighing 180 to 220 g, six animals per group) were subjected to the experiment after they had been fasted for 18 hours and further deprived of food and water for 3 hours.

After the rats were orally administered with test compounds suspended in a 0.9% saline solution at the dose of 25 ml/kg, each of them was put in a metabolic cage. The urine excreted within 6 hours after the administration was collected, and the urine volume and sodium (Na), potassium (K) and chlorine (Cl) ions were assayed. The urine sodium and potassium ions were measured by the flame spectrophotometry and the chlorine ions were measured by the chloride counter. The results are shown in Table 1.

The test compounds were the compounds described below in Examples and the following (as applies to the following Pharmacological Experimental Examples), and the compounds numbers respectively correspond to the compound numbers described at the end of the compound names recited in Examples and the following. In the table, each of the numerals represents average value±average error and the mark * designates that the value is statistically significant as compared with the control by $P<0.05$ and mark ** designates that the value is statistically signficant by $P<0.01$.

TABLE 1

| Test Compound | Dose (mg/kg, p.o.) | Urine Volume (ml/100 g body weight/ 6 hrs.) | Excretion of Electrolyte ($\mu$eq/100 g body weight/ 6 hrs.) | | | |
|---|---|---|---|---|---|---|
| | | | Na | K | Cl | Na/K |
| Compound (2) | 0 | 0.8 ± 0.1 | 134 ± 19 | 70 ± 7 | 170 ± 19 | 2.0 ± 0.3 |
| | 3.0 | 2.0 ± 0.2** | 284 ± 30** | 95 ± 7* | 349 ± 27** | 3.1 ± 0.3* |
| Compound (10) | 0 | 1.0 ± 0.3 | 148 ± 30 | 51 ± 8 | 169 ± 23 | 2.8 ± 0.2 |
| | 10.0 | 2.6 ± 0.3** | 402 ± 43** | 73 ± 8* | 379 ± 35** | 5.8 ± 0.7** |
| Compound (17) | 0 | 1.5 ± 0.2 | 212 ± 21 | 75 ± 7 | 256 ± 20 | 2.9 ± 0.4 |
| | 10.0 | 2.4 ± 0.2** | 346 ± 28** | 64 ± 4 | 358 ± 25** | 5.7 ± 0.9** |

PHARAMACOLOGICAL EXPERIMENTAL EXAMPLE 2

Action on coronary blood flow

A mongrel adult dog was anesthetized by intravenous administration with sodium pentobarbital at the dose of 30 mg/kg body weight. In accordance with the method by Yago et al [Folia pharmacologica japonica, vol. 57, p. 380 (1961)], the left coronary artery was perfused and the volume of blood flow was measured. The test compounds were administered in the coronary artery at a dosage of 10 to 30 $\mu$l. The effects of the test compounds on the coronary blood flow were represented by $ED_{50}$ ($\mu$g) which was determined as the dose required for increasing the coronary blood flow to the level of 50% of the effect which was attained by administering the coronary artery 3 $\mu$g of Nifedipine [dimethyl 2,6-dimethyl-4-(2-nitrophenyl)-1,4-dihydropyridine-3,5-dicarboxylate]. The results are tabulated in Table 2.

PHARMACOLOGICAL EXPERIMENTAL EXAMPLE 3

Action on vertebrarterial blood flow

After mongrel adult dog was anesthetized by intravenous administration of sodium pentobarbital at the dose of 25 mg/kg body weight, the right vertebrartery was perfused and the volume of blood flow was measured. The test compounds were administered in the vertebral artery.

With the maximum increase rate in the blood flow being taken as 100% when 100 $\mu$g of papaverine hydrochloride (1-[(3,4-dimethoxyphenyl)methyl]-6,7-dimethoxyisoquinoline hydrochloride) was administered in the vertebral artery, the effects of the test compounds were represented by $ED_{100}$ ($\mu$g) which denotes the dose required for attaining an increased rate of the blood flow of 100%. The results are indicated in Table 2.

TABLE 2

| Test Compound | Coronary vasodilating action, $ED_{50}$($\mu$g) | Vertebrarterial vasodilating action, $ED_{100}$($\mu$g) |
|---|---|---|
| Compound (4) | 12 | 63 |
| Compound (6) | 10 | 48 |
| Compound (8) | 63 | 58 |
| Compound (25) | 22 | 76 |

PHARMACOLOGICAL EXPERIMENTAL EXAMPLE 4

5-Lipoxygenase-inhibitory action

In accordance with the method of Ochi et al (J. Biol. Chem., vol. 258, pp. 5754–5758 (1983)), the 105,000×g supernatant fraction of intraperitoneal polymorph leukocyte of guinea pigs was prepared, and the capability of producing 5-hydroxyeicosatetraenoic acid (5-HETE) from arachidonic acid was assayed.

Male guinea pigs weighing about 500 g were intraperitoneally administered with 1/10 volume (at the dose of 10 ml/100 g body weight) of a 2% casein solution and operated in the abdomen 16–18 hours after the administration. The intraperitoneal effusion was taken and the insdie of the abdomen was washed with a saline solution containing 10 mM phosphate buffer solution (pH 7.4) twice. The obtained effusion and the washing solution were collected and centrifuged at 150×g for five minutes. A 0.2% saline solution was added to the sediment, followed by hypotonic treatment to subject the mixed erythrocyte to hemolysis. After a 1.6% saline solution was added thereto to make the mixture isotonic, it was centrifuged in the same manner and suspended in 50 mM Hepes buffer solution (pH 8.0). The suspension was treated with supersonic waves (by Branson sonifier, model 185) and centrifuged at 10,000×g for 10 minutes. The supernatant was further centrifuged at 105,000×g for 60 minutes. The supernatant thus obtained was taken as the 5-lipoxygenase fraction which was freezed to −70° C. to be preserved.

The reaction mixture was prepared in the total amount of 0.2 ml from 5-lipoxygenase fraction (0.5 mg protein), 3.4 $\mu$M [1-$^{14}$C] arachidonic acid (40 nCi, Amersham International), 1 mM potassium chloride, 2 mM ATP and 1 mM glutathion in 50 mM Tris-hydrochloride buffer solution (pH 7.3). The test compound dissolved in dimethylsulfoxide and the supernatant fraction were pre-incubated at 30° C. for 2 minutes. Afer $^{14}$C-arachidonic acid was added thereto, the mixture was incubated at 30° C. for 3 minutes. The reaction was terminated by adding 20 $\mu$l of 0.4M citric acid solution. The reaction mixture was extracted with 1 ml of ethyl ether, wherewith 0.5 g of anhydrous sodium sulfate was admixed. The mixture was lightly centrifuged. The supernatant (0.6 ml) was put in another test tube, which was evaporated to dryness. The residue was dissloved in 50 $\mu$l of chloroform-methanol (2:1), and the solution was spotted on the silica gel plate (Whatman, $LK_5DF$) where standard arachidonic acid, prostaglandin $B_2$, 5- and 12-HETE had in advance been spotted as the markers. The thin-layer chormatography was conducted by the use of ethyl ether-petroleum ether-acetic acid (85:15:0.1) as the developing solvent. The amount of the produced 5-HETE was assayed by means of the Linear analyzer (Berthold, model LB282).

As a result, the 50% inhibitory concentration of Compound (4) and Compound (25) against the production of 5-HETE ws respectively 20 $\mu$M and 19 $\mu$M.

Though ddY strain mice were intraperitoneally or orally administered with Compound (2) at the dose of 300 mg/kg, none of them was observed to die.

As shown in the foregoing Experimental Examples, the compounds of this invention are useful as diuretics and therapeutic medicines for chronic edema, hypertension, ischemic diseases in the brain and heart, thrombotic diseases, congestive heart diseases, cerebral and coronary-vasospasms and so on.

When the compounds of the present invention are used as the above-mentioned medicines, a therapeutically effective amount of the compounds of the present invention are, if suitable, in an admixture with a pharmacologically acceptable pharmaceutical additives (carriers, excipients, diluents and so on), formed into powders, granules, tablets, capsules and injectable preparations, which can be administered orally or parenterally. While the dose varies depending upon target diseases to be treated, symptoms, compounds to be administered, when orally administered, the dose is generally about 1 mg to 500 mg daily per adult.

PHARMACEUTICAL FORMULATION EXAMPLE

The tablet containing 5 mg of the compound of the present invention can be prepared by the following formulation.

| | |
|---|---|
| Compound (2) | 5.0 mg |
| Corn starch | 15.0 mg |
| Lactose | 60.0 mg |
| Fine crystalline cellulose | 16.0 mg |
| Talc | 3.0 mg |
| Magnesium stearate | 1.0 mg |
| | 100.0 mg |

The tablet can be, if desired, made sugar-coated or film-coated tablet.

EXAMPLE

The present invention is concretely described below by illustrating Working Examples, which are not to be construed as limitative.

EXAMPLE 1

4-(5-Hydroxy-2-methyl-4-piperidinomethyl-1H-indol-3-ylcarbonyl)morphopine [Compound (1)]

Piperidine (2 g) and 1.9 g of a 37% formalin were added to a solution of 5 g of 4-(5-hydroxy-2-methyl-1H-indol-3-ylcarbonyl)morpholine in 100 ml of acetic acid, and after the mixture was stirred at 60° C. for 4 hours, the acetic acid was distilled off under reduced pressure. Ethyl acetate and water were added to the residue, which was made alkaline with potassium carbonate to separate crystals. The crystals were collected by filtration and recrystallized from ethyl acetate-methanol to give 2.3 g of the titled compound in the form of white crystals, m.p. 232°-238° C. (decomposition).

EXAMPLE 2

4-(6-Bromo-5-hydroxy-2-methyl-4-piperidinomethyl-1H-indol-3-ylcarbonyl)morpholine [Compound (2)]

Bromine (2.3 g) was dropwise added to a solution of 5 g of Compound (1) in 50 ml of acetic acid at the temperature of 15° C. After the mixture was stirred at room temperature for two hours, isopropyl ether was added. Water was added to the separated oily substance, which was made alkaline with potassium carbonate, followed by extraction with chloroform. After the organic layer was washed with water and dried, the solvent was distilled off. Ethyl acetate was added to the residue to separate crystals. The crystals were collected by filration and recrystallized from methanol to give 2.8 g of the titled compound as white crystals, m.p. 216°-218° C. (decomposition).

EXAMPLE 3

N,N-Dibutyl-5-hydroxy-2-methyl-1-(2-phenylethyl)-4-piperidinomethylindole-3-carboxamide [Compound (3)]

Piperidine (11 g) and 11 g of 37% formalin were added to a solution of 44 g of N,N-dibutyl-5-hydroxy-2-methyl-1-(2-phenylethyl)indole-3-carboxamide in 20 m of acetic acid, and the mixture was stirred at 60° C. for 2 hours. The acetic acid was distilled off under reduced pressure. Water was added to the residue, which was made alkaline with potassium carbonate, followed by extraction with ethyl acetate. After the organic layer was washed with water and dried, the solvent was distilled off. Hexane was added to the residue to separate crystals. The crystals were collected by filtration and recrystallized from isopropyl ether to give 31 g of the titled compound as white crystals, m.p. 105°-107° C.

EXAMPLE 4

N,N-Dibutyl-5-hydroxy-2-methyl-1-(2-phenylethyl)-4-piperidinomethyl-6-propionylindole-3-carboxamide [Compound (4)]

Anhydrous aluminum chloride (8.6 g), 6 g of propionyl chloride and 13 g of Compound (3) were added to 100 ml of dichloroethane, and the mixture was heated under reflux for 5 hours. The reaction mixture was added to ice water, which was extracted with chloroform. Potassium carbonate was added to the extracted layer and the mixture was stirred for 30 minutes. After the organic layer was washed with water and dried, the solvent was distilled off. Petroleum ether was added to the residue to separate crystals. The crystals were collected by filtration and recrystallized twice from hexane to give 7.7 g of the titled compound as yellow crystals, m.p. 111°-112° C.

EXAMPLE 5

N,N-Dibutyl-1-hexyl-5-hydroxy-2-methyl-4-piperidinomethylindole-3-carboxamide hydrochloride [Compound (5)]

Piperidine (10.6 g) and 10.4 g of 37% formalin were added to a solution of 43.7 g of N,N-dibutyl-1-hexyl-5-hydroxy-2-methylindole-3-carboxamide in 200 ml of acetic acid, and the mixtue was stirred at 60° C. for 2 hours. The acetic acid was distilled off under reduced pressure. Water was added tothe residue, which was made alkaline with potassium carbonate, followed by extraction with ethyl acetate. After the organic layer was washed with water and dried, the solvent was distilled off. The residue was converted to the hydrochloride with the use of ethanolhydrochloric acid, followed by recrystallization from acetone to give 22 g of the titled compound as white crystals, m.p. 170°-171° C. (decomposition).

EXAMPLE 6

N,N-dibutyl-1-hexyl-5-hydroxy-2-methyl-4-piperidinomethyl-6-propionylindole-3-carboxamide [Compound (6)]

Anhydrous aluminum chloride (6.4 g), 4.4 g of propionyl chloride and 10 g of Compound (5) were added to 100 ml of dichloroethane, and the mixture was heated under reflux for 5 hours. The reaction mixture was poured into ice-water, followed by extraction with chloroform. An aqueous solution of potassium carbonate was added to the extracted layer, and the mixture was stirred for 30 minutes. After the organic layer was washed wtih water and dried, the solvent was distilled off. Hexane was added to the residue to separate crystals. The crystals were collected by filtration and recrystallized from isopropyl ether to give 7.9 g of the titled compound as yellow crystals, m.p. 124°–125° C.

By the same manner as the above-mentioned Example 1 to 6, for example, the following compounds can be produced.

(7) 4-(6-Acetyl-5-hydroxy-2-methyl-4-piperidinomethyl-1H-indol-3-ylcarbonyl)morpholine [Compound (7)], m.p. 226°–228° C. (decomposition)

(8) 1,N-Dibutyl-5-hydroxy-2-methyl-4-piperidinomethylindole-3-carboxamide [Compound (8)], m.p. 108°–110° C.

(9) 6-Bromo-1,N-dibutyl-5-hydroxy-2-methyl-4-piperidinomethylindole-3-carboxamide [Compound (9)], m.p. 135°–137° C.

(10) 6-Bromo-N-butyl-5-hydroxy-2-methyl-4-piperidinomethylindole-3-carboxamide [Compound (10)], m.p. 202°–203° C. (decomposition)

(11) 4-[6-Bromo-5-hydroxy-2-methyl-1-(2-phenylethyl)-4-piperidinomethylindol-3-ylcarbonyl]morpholine [Compound (11)], m.p. 215°–217° C. (decomposition)

(12) 4-[5-Hydroxy-2-methyl-1-(2-phenylethyl)-4-piperidinomethylindol-3-ylcarbonyl]morpholine [Compound (12)], m.p. 167°–169° C.

(13) 4-[6-Acetyl-5-hydroxy-2-methyl-1-(2-phenylethyl)-4-piperidinomethylindol-3-ylcarbonyl]morpholine [Compound (13)], m.p. 174°–175° C.

(14) 4-(1-Butyl-5-hydroxy-2-methyl-4-piperidinomethylindol-3-ylcarbonyl)morpholine [Compound (14)], m.p. 150°–152° C.

(15) 4-(6-Bromo-1-butyl-5-hydroxy-2-methyl-4-piperidinomethylindol-3-ylcarbonyl)morpholine [Compound (15)], m.p. 156°–158° C.

(16) 5-Hydroxy-2-methyl-N-octyl-1-(2-phenylethyl)-4-piperidinomethylindole-3-carboxamide [Compound (16)], m.p. 109°–111° C.

(17) N,N-Dibutyl-5-hydroxy-2-methyl-4-piperidinomethylindole-3-carboxamide [Compound (17)], m.p. 157°–159° C.

(18) 6-Bromo-N,N-dibutyl-5-hydroxy-2-methyl-4-piperidinomethylindole-3-carboxamide [Compound (18)], m.p. 213°–215° C. (decomposition)

(19) 1-(6-Bromo-5-hydroxy-2-methyl-4-piperidinomethyl-1H-indol-3-ylcarbonyl)piperidine [Compound (19)], m.p. 174°–176° C. (decomposition)

(20) N,N-Dibutyl-5-hydroxy-2-methyl-1-phenyl-4-piperidinomethylindole-3-carboxamide [Compound (20)], m.p. 143°–144° C.

(21) 6-Acetyl-N,N-dibutyl-5-hydroxy-2-methyl-1-phenyl-4-piperidinomethylindole-3-carboxamide [Compound (21)], m.p. 136°–138° C.

(22) 6-Bromo-N,N-dibutyl-5-hydroxy-2-methyl-1-phenyl-4-piperidinomethylindole-3-carboxamide [Compound (22)], m.p. 183°–184° C.

(23) 6-Acetyl-5-hydroxy-2-methyl-N-octyl-1-phenyl-4-piperidinomethylindole-3-carboxamide [Compound (23)], m.p. 143°–145° C.

(24) 6-Bromo-N,N-dibutyl-5-hydroxy-2-methyl-1-(2-phenylethyl)-4-piperidinomethylindole-3-carboxamide [Compound (24)], m.p. 115°–116° C.

(25) N,N-Dibutyl-5-hydroxy-2-methyl-1-phenyl-4-piperidinomethyl-6-propionylindole-3-carboxamide [Compound (25)], m.p. 115°–116° C.

(26) 6-Bromo-5-hydroxy-2-methyl-N-octyl-1-phenyl-4-piperidinomethylindole-3-carboxamide [Compound (26)], m.p. 204°–206° C. (decomposition)

(27) 5-Hydroxy-2-methyl-N-octyl-1-phenyl-4-piperidinomethylindole-3-carboxamide hydrochloride [Compound (27)], m.p. 198°–199° C.

(28) 6-Bromo-N,N-dibutyl-1-hexyl-5-hydroxy-2-methyl-4-piperidinomethylindole-3-carboxamide [Compound (28)], m.p. 92°–93° C.

(29) 1,N-Dibutyl-5-hydroxy-2-methyl-4-piperidinomethyl-6-propionylindole-3-carboxamide [Compound (29)], m.p. 135°–136° C.

(30) N-Butyl-1-hexyl-5-hydroxy-2-methyl-4-piperidinomethylindole-3-carboxamide [Compound (30)], m.p. 120°–121° C.

(31) N-Butyl-1-hexyl-5-hydroxy-2-methyl-4-piperidinomethyl-6-propionylindole-3-carboxamide [Compound (31)], m.p. 174°–175° C.

(32) 1-Benzyl-5-hydroxy-2-methyl-N-octyl-4-piperidinomethylindole-3-carboxamide [Compound (32)], m.p. 144°–146° C.

(33) 1-Benzyl-5-hydroxy-2-methyl-N-octyl-4-piperidinomethyl-6-propionylindole-3-carboxamide hydrochloride monohydrate [Compound (33)], m.p. 199°–200° C. (decomposition)

(34) N-Pentyl-5-hydroxy-2-methyl-1-phenyl-4-piperidinomethylindole-3-carboxamide hydrochloride [Compound (34)], m.p. 226°–228° C. (decomposition)

(35) N-Butyl-5-hydroxy-2-methyl-1-phenyl-4-piperidinomethylindole-3-carboxamide [Compound (35)], m.p. 158°–160° C.

(36) 1-Hexyl-5-hydroxy-2-methyl-4-piperidinomethyl-N-(4-pyridyl)indole-3-carboxamide [Compound (36)], m.p. 193°–194° C. (decomposition)

(37) 5-Hydroxy-2-methyl-N-pentyl-1-phenyl-4-piperidinomethyl-6-propionylindole-3-carboxamide hydrochloride [Compound (37)], m.p. 224°–226° C. (decomposition)

(38) 5-Hydroxy-2-methyl-1-phenyl-4-piperidinomethyl-N-(4-pyridyl)indole-3-carboxamide [Compound (38)], m.p. 178°–180° C.

(39) 6-Bromo-5-hydroxy-2-methyl-1-phenyl-4-piperidinomethyl-N-(4-pyridyl)indole-3-carboxamide [Compound (39)], m.p. 209°–211° C. (decomposition)

(40) 1-Hexyl-5-hydroxy-2-methyl-4-piperidinomethylindole-3-carboxamide [Compound (40)], m.p. 174°–175° C.

(41) N-Hexyl-5-hydroxy-2-methyl-1-phenyl-4-piperidinomethylindole-3-carboxamide [Compound (41)], m.p. 152°–154° C.

(42) 1,N-Diphenyl-5-hydroxy-2-methyl-4-piperidinomethylindole-3-carboxamide [Compound (42)], m.p. 157°–159° C.

(43) 5-Hydroxy-2-methyl-1-phenyl-N-(2-phenylethyl)-4-piperidinomethylindole-3-carboxamide [Compound (43)], m.p. 180°–182° C.

(44) 6-Bromo-1-hexyl-5-hydroxy-2-methyl-4-piperidinomethylindole-3-carboxamide [Compound (44)], m.p. 157°–158° C.

(45) 1-Hexyl-5-hydroxy-2-methyl-N-pentyl-4-piperidinomethylindole-3-carboxamide [Compound (45)], m.p. 140°–141° C.

(46) 1-Hexyl-5-hydroxy-2-methyl-N-phenyl-4-piperidinomethylindole-3-carboxamide [Compound (46)], m.p. 138°–140° C.

(47) 1-Hexyl-5-hydroxy-2-methyl-N-(2-phenylethyl)-4-piperidinomethylindole-3-carboxamide [Compound (47)], m.p. 98°–100° C.

(48) 1,N-Diphenyl-5-hydroxy-2-methyl-4-piperidinomethyl-6-propionylindole-3-carboxamide hydrochloride [Compound (48)], m.p. 237°–239° C. (decomposition)

(49) 2,N-Dimethyl-N-benzyl-5-hydroxy-1-phenyl-4-piperidinomethylindole-3-carboxamide [Compound (49)], m.p. 162°–164° C.

(50) 5-Hydroxy-2-methyl-1-phenyl-N-(2-phenylethyl)-4-piperidinomethyl-6-propionylindole-3-carboxamide hydrochloride [Compound (50)], m.p. 209°–211° C. (decomposition)

(51) 1-Hexyl-5-hydroxy-2-methyl-N-phenyl-4-piperidinomethyl-6-propionylindole-3-carboxamide [Compound (51)], m.p. 203°–204° C.

(52) 2,N-Dimethyl-1-hexyl-5-hydroxy-N-octyl-4-piperidinomethylindole-3-carboxamide hydrochloride [Compound (52)], m.p. 177°–178° C. (decomposition)

(53) 2,N-Dimethyl-1-hexyl-5-hydroxy-N-octyl-4-piperidinomethyl-6-propionylindole-3-carboxamide [Compound (53)], m.p. 119°–120° C.

(54) N,N-Diethyl-1-hexyl-5-hydroxy-2-methyl-4-piperidinomethyl-6-propionylindole-3-carboxamide [Compound (54)], m.p. 154°–155° C.

(55) N-Benzyl-2,N-dimethyl-1-hexyl-5-hydroxy-4-piperidinomethyl-6-propionylindole-3-carboxamide [Compound (55)], m.p. 116°–117° C.

(56) 5-Hydroxy-2-methyl-1-(4-methylphenyl)-N-octyl-4-piperidinomethyl-6-propionylindole-3-carboxamide [Compound (56)], m.p. 127°–128° C.

The present invention has been described in detail in the foregoing specification including Working Examples, which can be modified and varied to such an extent as not to conflict with the concept and the scope of the present invention.

We claim:

1. A 5-hydroxyindole-3-carboxylic acid amide compound of the general formula:

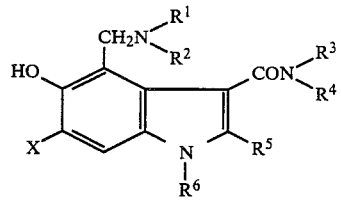

wherein $R^1$, $R^2$, $R^3$ and $R^4$ are, the same or different, respectively a hydrogen atom, an alkyl group, an aryl group, an aralkyl group or a heteroaryl group, or $R^1$ and $R^2$ and/or $R^3$ and $R^4$ are respectively groups which are combined to each other taken together with the adjacent nitrogen atom to form a heterocyclic group, $R^5$ is an alkyl group, $R^6$ is a hydrogen atom, an alkyl group, a cycloalkyl group, an aryl group or an aralkyl group and X is a hydrogn atom, a halogen atom or a lower alkanoyl group, or its acid addition salt.

2. A compound as claimed in claim 1 wherein $R^1$ and $R^2$ are groups which are combined to each other taken together with the adjacent nitrogen atom to from piperidine.

3. A compound as claimed in claim 1 which is selected from among 4-(5-hydroxy-2-methyl-4-piperidinomethylindol-3-ylcarbonyl)morpholine, 4-(6-bromo-5-hydroxy-2-methyl-4-piperidinomethylindol-3-ylcarbonyl)morpholine, N,N-dibutyl-5-hydroxy-2-methyl-1-(2-phenylethyl)-4-piperidinomethylindole-3-carboxamide, N,N-dibutyl-5-hydroxy-2-methyl-1-(2-phenylethyl)-4-piperidinomethyl-6-propionylindole-3-carboxamide, N,N-dibutyl-1-hexyl-5-hydroxy-2-methyl-4-piperidinomethyl-6-propionylindole-3-carboxamide, 1,N-dibutyl-5-hydroxy-2-methyl-4-piperidinomethylindole-3-carboxamide, 6-bromo-1,N-dibutyl-5-hydroxy-2-methyl-4-piperidinomethylindole-3-carboxamide, 6-bromo-N-butyl-5-hydroxy-2-methyl-4-piperidinomethylindole-3-carboxamide, 4-[6-bromo-5-hydroxy-2-methyl-1-(2-phenylethyl)-4-piperidinomethylindol-3-ylcarbonyl]morpholine, 4-(6-bromo-1-butyl-5-hydroxy-2-methyl-4-piperidinomethylindol-3-ylcarbonyl)morpholine, N,N-dibutyl-5-hydroxy-2-methyl-4-piperidinomethylindole-3-carboxamide, 6-bromo-N,N-dibutyl-5-hydroxy-2-methyl-4-piperidinomethylindole-3-carboxamide, 1-(6-bromo-5-hydroxy-2-methyl-4-piperidinomethylindol-3-ylcarbonyl)piperidine and N,N-dibutyl-5-hydroxy-2-methyl-1-phenyl-4-piperidinomethyl-6-propionylindole-3-carboxamide or their acid addition salts.

4. 4-(6-Bromo-5-hydroxy-2-methyl-4-piperidinomethyl-1H-indol-3-ylcarbonyl)morpholine.

5. A pharmaceutical compositin comprising a compound as claimed in claim 1 and a pharmaceutically acceptable additive.

6. A diuretic which comprises a compound as claimed in claim 1 and a pharmaceutically acceptable additive.

* * * * *